United States Patent
Palani et al.

(10) Patent No.: US 7,345,042 B2
(45) Date of Patent: Mar. 18, 2008

(54) MCH ANTAGONISTS FOR THE TREATMENT OF OBESITY

(75) Inventors: Anandan Palani, Bridgewater, NJ (US); Sherry A. Shapiro, Belford, NJ (US); Hubert B. Josien, Hoboken, NJ (US); Thomas A. Bara, Linden, NJ (US); John W. Clader, Cranford, NJ (US); Pradeep B. Pushpavanam, Kendall Park, NJ (US); Shengjian Li, Belle Mead, NJ (US); Mark D. McBriar, Annandale, NJ (US)

(73) Assignee: Schering Corporation, Kenilworth, NJ (US)

( * ) Notice: Subject to any disclaimer, the term of this patent is extended or adjusted under 35 U.S.C. 154(b) by 403 days.

(21) Appl. No.: 10/878,788

(22) Filed: Jun. 28, 2004

(65) Prior Publication Data
US 2005/0004121 A1    Jan. 6, 2005

Related U.S. Application Data

(60) Provisional application No. 60/483,619, filed on Jun. 30, 2003.

(51) Int. Cl.
*A61K 31/496*    (2006.01)
*C07D 409/14*    (2006.01)

(52) U.S. Cl. .................. 514/253.11; 544/364
(58) Field of Classification Search ........... 514/253.11; 544/364
See application file for complete search history.

(56) References Cited

U.S. PATENT DOCUMENTS
6,391,865 B1 *    5/2002    Baroudy et al. .............. 514/63

OTHER PUBLICATIONS
Vippagunta et al. Advanced Drug Delivery Reviews, vol. 48, p. 3-26 (2001).*

* cited by examiner

*Primary Examiner*—Emily Bernhardt
(74) *Attorney, Agent, or Firm*—William Y. Lee; Palaiyur S. Kalyanaraman

(57) ABSTRACT

The present invention discloses methods of using antagonists for melanin-concentrating hormone (MCH), to treat obesity, metabolic disorders, eating disorders such as hyperphagia, and diabetes, as well as novel compounds which are antagonists for melanin-concentrating hormone (MCH). In other aspects, the invention is directed to pharmaceutical compositions comprising such MCH antagonists as well as methods for preparing such compounds. Compounds of the invention generally have the structure:

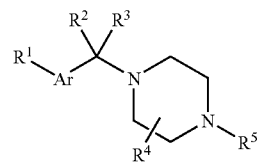

where the substituents are as defined herein.

6 Claims, No Drawings

MCH ANTAGONISTS FOR THE TREATMENT OF OBESITY

CROSS REFERENCE TO RELATED APPLICATIONS

This application claims the benefit of U.S. Provisional Application No. 60/483,619 filed on Jun. 30, 2003.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670-673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., *Nature Medicine,* 8, pp. 825-830 (01 Aug. 2002). Substituted benzyl-piperazines that act as muscarinic antagonists are disclosed in U.S. Pat. No. 5,883,096, U.S. Pat. No. 5,889,006, U.S. Pat. No. 6,037,352, U.S. Pat. No. 6,043,255, U.S. Pat. No. 6,288,068 and U.S. Pat. No. 6,498,168.

SUMMARY OF THE INVENTION

In one embodiment, this invention provides a method of treatment comprising adminstering compounds having MCH antagonist activity represented by structural formula I:

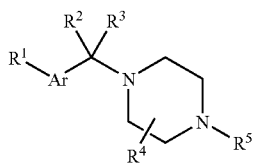

I or a pharmaceutically acceptable salt or solvate of said compound, isomer or racemic mixture to a patient in need of such treatment, wherein Ar is aryl, $R^{11}$-substituted aryl, heteroaryl, $R^{11}$-substituted heteroaryl, heteroaralkyl or $R^{11}$-substituted heteroaralkyl;

$R^1$ is —C(O)-aryl, —O-alkyl, halo, aryl, $R^{10}$-substituted aryl, heteroaryl, $R^{10}$-substituted heteroaryl, heteroaralkyl, $R^{10}$-substituted heteroaralkyl, alkyl, $R^{10}$-substituted alkyl, aralkyl, $R^{10}$-substituted aralkyl,

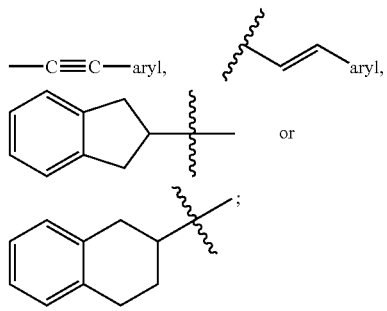

$R^2$ and $R^3$ are each independently selected from the group consisting of hydrogen, alkyl, aryl and heteroaryl;

$R^4$ is hydrogen or alkyl;

$R^5$ is alkyl, aryl, cycloalkyl,

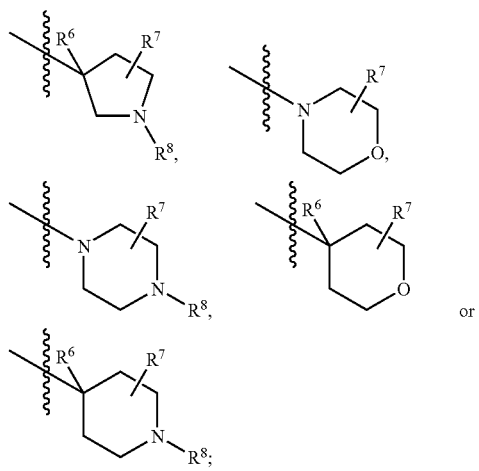

$R^6$ is hydrogen, alkyl, $R^{10}$-substituted alkyl or alkenyl;

$R^7$ is hydrogen or $R^7$ is 1 to 3 subsitutents, each $R^7$ being independently selected from alkyl or $R^{10}$-substituted alkyl;

$R^8$ is hydrogen, alkyl, —C(O)O-alkyl, —C(O)N-alkyl, —C(O)N-aryl or —C(O)$R^9$;

$R^9$ is aryl, $R^{10}$-substituted aryl, heteroaryl or $R^{10}$-substituted heteroaryl;

$R^{10}$ is one to four moieties, each $R^{10}$ can be the same or different and each $R^{10}$ is independently selected from the group consisting of alkoxy, alkyl, aryl, aralkyl, cycloalkyl, cycloalkylalkyl-, haloalkoxy, haloalkyl, halo, heterocyclyl, heteroaryl, —CF$_3$, —CN, —C(O)N($R^2$)$_2$, —C(O)$R^2$, —C(O)O$R^2$, —NC(O)$R^2$, —NC(O)O$R^2$, —NC(O)N($R^2$)$_2$, —NC(=N—CN)NHR$^2$, —NO$_2$, —N($R^2$)$_2$, —OH, —S(O$^2$)$R^2$ and —S(O$_2$)N($R^2$)$_2$ or two $R^{10}$ moieties on adjacent carbons can be joined together to form a methylenedioxy or ethylenedioxy group;

and $R^{11}$ is hydrogen, alkyl, haloalkyl, alkoxy or halo.

This invention is also directed to pharmaceutical compositions comprising at least one compound of formula I, or a pharmaceutically acceptable salt or solvate of said compound, for the treatment of metabolic disorders such as obesity, and eating disorders such as hyperphagia. In one aspect, this invention is also directed to pharmaceutical compositions for the treatment of obesity which comprise an obesity treating amount of a compound of formula I, or a pharmaceutically acceptable salt or solvate of said compound and a pharmaceutically acceptable carrier.

DETAILED DESCRIPTION

The present invention relates to the use of one or more compounds that are represented by structural formula I, or a pharmaceutically acceptable salt or solvate thereof, wherein the various moieties are as described above.

One aspect of the invention is a method of treating metabolic disorders, eating disorders or diabetes with at least one compound of formula I that has the structure

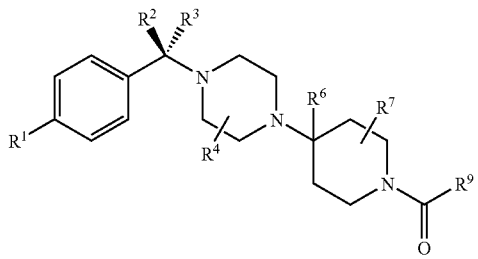

$R^1$ is —C(O)-aryl, —O-alkyl, halo, aryl, $R^{10}$-substituted aryl, heteroaryl, $R^{10}$-substituted heteroaryl, heteroaralkyl, $R^{10}$-substituted heteroaralkyl, alkyl, $R^{10}$-substituted alkyl, aralkyl, $R^{10}$-substituted aralkyl,

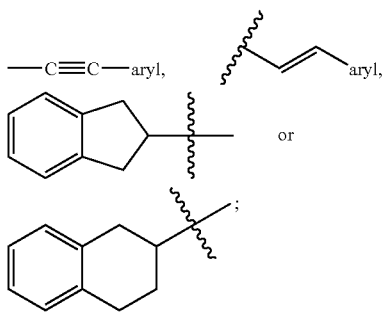

$R^2$ and $R^3$ are hydrogen, alkyl or aryl;
$R^4$ is hydrogen or alkyl;
$R^7$ is hydrogen or $R^7$ is subsitutent independently selected from alkyl or $R^{10}$-substituted alkyl;
$R^9$ is aryl, $R^{10}$-substituted aryl, heteroaryl or $R^{10}$-substituted heteroaryl;
and
$R^{10}$ is defined as above.

In additional aspects of the above method of treatment, the compound of formula I is used wherein
$R^1$ is aryl, $R^{10}$-substituted aryl, heteroayl, $R^{10}$-substituted heteroaryl, aralkyl, $R^{10}$-substituted aralkyl, heteroaralkyl or $R^{10}$-substituted heteroaralkyl;
$R^2$ is hydrogen;
$R^3$ is methyl;
$R^4$ is hydrogen or methyl;

$R^5$ is

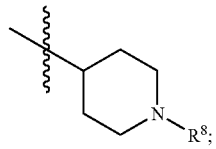

$R^8$ is —C(O)$R^9$;
and
$R^9$ is heteroaryl or $R^{10}$-substituted heteroaryl.

Additional aspects of the above method of treatment include those methods where the compound of formula I has the structure:

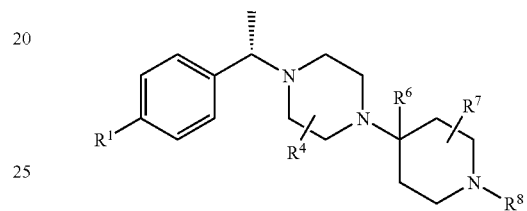

wherein
$R^1$ is selected from the group consisting of

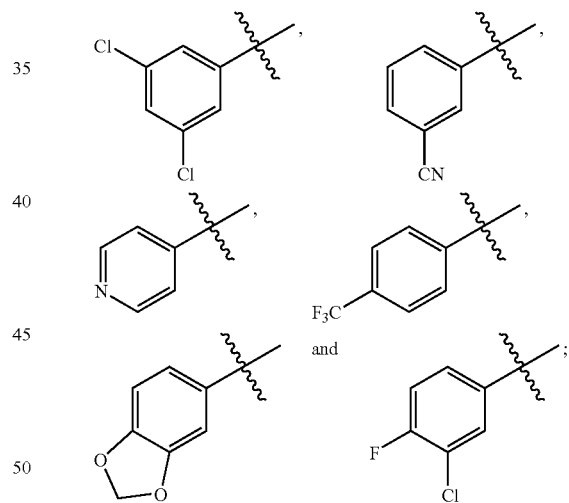

$R^4$, $R^6$ and $R^7$ are methyl;
$R^8$ is —C(O)$R^9$;
$R^9$ is

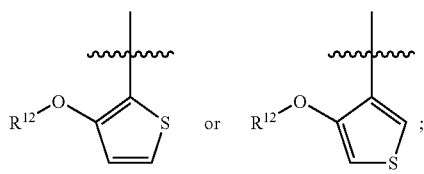

and
$R^{12}$ is ethyl, propyl, butyl or cyclopropylmethyl.

Another aspect of the above method of treatment includes using compounds of formula I wherein $R^9$ is

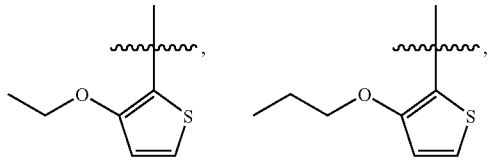

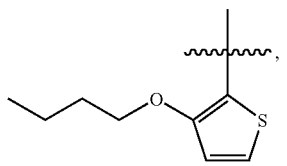

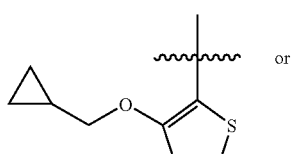

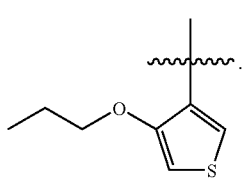

Other embodiments of formula I include the method of treatment where the compound of formula I is selected from the group consisting of Examples 1-20.

Other embodiments of the claimed invention include those methods of treatment with the compounds of formula I wherein the eating disorder is hyperphagia and wherein the metabolic disorder is obesity.

Another embodiment is a method of treating a disorder associated with obesity comprising administering to a mammal in need of such treatment a therapeutically effective amount of at least one compound of formula I, or a pharmaceutically acceptable salt or solvate of said compound. Specific examples of disorders associated with obesity include but are not limited to type II diabetes, insulin resistance, hyperlipidemia or hypertension.

Another embodiment includes a method of treating an eating disorder which comprises administering to a mammal in need of such treatment an amount of a first compound, said first compound being a compound of formula I or a pharmaceutically acceptable salt or solvate of said compound;

and a second compound, said second compound being an antiobesity and/or anorectic agent selected from the group consisting of a $\beta_3$ agonist, a thryomimetic agent, an anorectic agent and an NPY antagonist;

wherein the amounts of the first and second compounds result in the desired effect.

Other embodiments of the invention are compounds of formula I having the following structure:

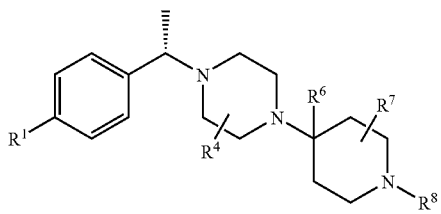

wherein
$R^1$ is selected from the group consisting of

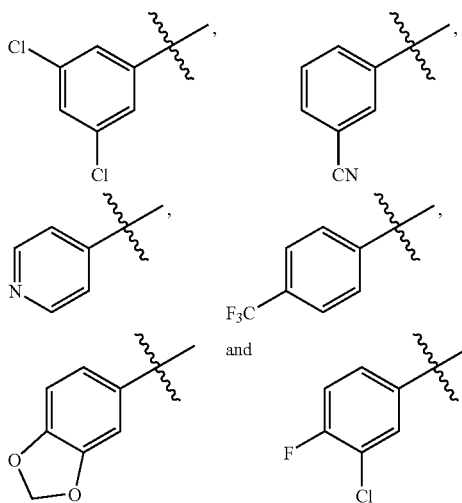

$R^4$, $R^6$ and $R^7$ are methyl;
$R^8$ is —C(O)$R^9$;
$R^9$ is

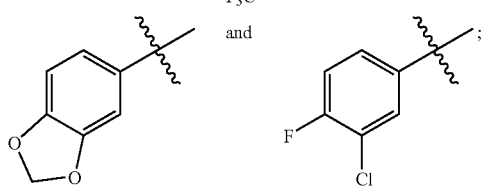

and
$R^{12}$ is ethyl, propyl, butyl or cyclopropylmethyl.

Still additional preferred embodiments of formula I include compounds selected from the group consisting of Examples 1-20.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. Non-limiting examples of suitable alkenyl groups include ethenyl, propenyl, n-butenyl, and 3-methylbut-2-enyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen. Non-limiting examples of suitable alkoxy groups include propoxy, ethoxy and butoxy.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from $R^{10}$. Further, when $R^2$, $R^3$, $R^4$, $R^5$, $R^8$ and $R^{11}$ are alkyl, said alkyl groups may optionally be substituted with the group consisting of alkyl, alkylheteroaryl, aryl, aralkyl, aralkenyl, heteroaralkenyl, heteroaryl, heteroaralkyl, hydroxy, hydroxyalkyl, alkoxy, aryloxy, aralkoxy, acyl, aroyl, halo, nitro, cyano, carboxy, alkoxycarbonyl, alkoxycarbonylalkylenyl, aryloxycarbonyl, aralkoxycarbonyl, arylsulfinyl, alkylsulfonyl, arylsulfonyl, heteroarylsulfinyl, heteroarylsulfonyl, alkylthio, arylthio, heteroarylthio, aralkylthio, heteroaralkylthio, cycloalkyl, cycloalkenyl, heterocyclyl, trifluoromethyl, $Y_1Y_2N$—, $Y_1Y_2N$-alkyl-, $Y_1C(O)N$—, $Y_1Y_2NC(O)$— and $Y_1Y_2NS(O)_2$—, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group. Non-limiting examples of suitable alkyl groups include methyl, ethyl, n-propyl, isopropyl, n-butyl, and t-butyl.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. Included in the definition of aryl are fused aryls such as indenyl, napthalenyl, anthracenyl and indolinyl. Fused aryls can be attached to the parent moiety either through the saturated or unsaturated portions of the ring. The aryl group can be unsubstituted or substituted on the ring with one or more substituents which may be the same or different, each being independently selected from $R^{10}$ or $R^{11}$. Further, when $R^2$, $R^3$ and $R^5$ are aryl, said aryl groups may optionally be substituted with the group consisting of alkyl, alkylheteroaryl, aryl, aralkyl, aralkenyl, heteroaralkenyl, heteroaryl, heteroaralkyl, hydroxy, hydroxyalkyl, alkoxy, aryloxy, aralkoxy, acyl, aroyl, halo, nitro, cyano, carboxy, alkoxycarbonyl, alkoxycarbonylalkylenyl, aryloxycarbonyl, aralkoxycarbonyl, arylsulfinyl, alkylsulfonyl, arylsulfonyl, heteroarylsulfinyl, heteroarylsulfonyl, alkylthio, arylthio, heteroarylthio, aralkylthio, heteroaralkylthio, cycloalkyl, cycloalkenyl, heterocyclyl, trifluoromethyl, $Y_1Y_2N$—, $Y_1Y_2N$-alkyl-, $Y_1C(O)N$—, $Y_1Y_2NC(O)$— and $Y_1Y_2NS(O)_2$—, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from $R^{10}$.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkoxy, alkyl, aryl, aralkyl, cycloalkyl, cycloalkylalkyl-, haloalkoxy, haloalkyl, halo, heterocyclyl, heteroaryl, —$CF_3$, —CN, —$C(O)N(R^2)_2$, —$C(O)R^2$, —$C(O)OR^2$, —$NC(O)R^2$, —NC$(O)OR^2$, —$NC(O)N(R^2)_2$, —NC(=N—CN)NHR$^2$, —$NO_2$, —$N(R^2)_2$, —OH, —$S(O_2)R^2$ and —$S(O_2)N(R^2)_2$ or two $R^{10}$ moieties on adjacent carbons can be joined together to form a methylenedioxy or ethylenedioxy group. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Halo" means fluoro, chloro, bromo or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl. The "heteroaralkyl" can be optionally substituted on the ring by replacing an available hydrogen on the ring by one or more substituents which may be the same or different, each being independently selected from $R^{10}$ or $R^{11}$.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from $R^{10}$ or $R^{11}$. A nitrogen atom of a heteroaryl can be optionally oxidized to the corresponding N-oxide. Further, when $R^2$ and $R^3$ are heteroaryl, said heteroaryl groups may optionally be substituted with the group consisting of alkyl, alkylheteroaryl, aryl, aralkyl, aralkenyl, heteroaralkenyl, heteroaryl, heteroaralkyl, hydroxy, hydroxyalkyl, alkoxy, aryloxy, aralkoxy, acyl, aroyl, halo, nitro, cyano, carboxy, alkoxycarbonyl, alkoxycarbonylalkylenyl, aryloxycarbonyl, aralkoxycarbonyl, arylsulfinyl, alkylsulfonyl, arylsulfonyl, heteroarylsulfinyl, heteroarylsulfonyl, alkylthio, arylthio, heteroarylthio, aralkylthio, heteroaralkylthio, cycloalkyl, cycloalkenyl, heterocyclyl, trifluoromethyl, $Y_1Y_2N-$, $Y_1Y_2N$-alkyl-, $Y_1C(O)N-$, $Y_1Y_2NC(O)-$ and $Y_1Y_2NS(O)_2-$, wherein $Y_1$ and $Y_2$ may be the same or different and are independently selected from the group consisting of hydrogen, alkyl, aryl, and aralkyl or two substituent groups on adjacent carbons can be joined together to form a methylenedioxy or ethylenedioxy group. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring or hydrogen(s) on any nitrogen(s) suitably by one or more substituents which may be the same or different, each being independently selected from the group consisting of alkoxy, alkyl, aryl, aralkyl, cycloalkyl, cycloalkylalkyl-, haloalkoxy, haloalkyl, halo, heterocyclyl, heteroaryl, $-CF_3$, $-CN$, $-C(O)N(R^2)_2$, $-C(O)R^2$, $-C(O)OR^2$, $-NC(O)R^2$, $-NC(O)OR^2$, $-NC(O)N(R^2)_2$, $-NC(=N-CN)NHR^2$, $-NO_2$, $-N(R^2)_2$, $-OH$, $-S(O_2)R^2$ and $-S(O_2)N(R^2)_2$ or two $R^{10}$ moieties on adjacent carbons can be joined together to form a methylenedioxy or ethylenedioxy group. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, thiophenyl, tetrahydrothiophenyl, morpholinyl and the like.

"Ring system substituent" means a substituent attached to an aromatic or non-aromatic ring system, which, for example, replaces an available hydrogen on the ring system. Ring system substituents may be the same or different, each being independently selected from the group consisting of alkoxy, alkyl, aryl, aralkyl, cycloalkyl, cycloalkylalkyl-, haloalkoxy, haloalkyl, halo, heterocyclyl, heteroaryl, $-CF_3$, $-CN$, $-C(O)N(R^2)_2$, $-C(O)R^2$, $-C(O)OR^2$, $-NC(O)R^2$, $-NC(O)OR^2$, $-NC(O)N(R^2)_2$, $-NC(=N-CN)NHR^2$, $-NO_2$, $-N(R^2)_2$, $-OH$, $-S(O_2)R^2$ and $-S(O_2)N(R^2)_2$ or two $R^{10}$ moieties on adjacent carbons can be joined together to form a methylenedioxy or ethylenedioxy group.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Aryloxy" means an aryl-O— group in which the aryl group is as previously described. Non-limiting examples of suitable aryloxy groups include phenoxy and naphthoxy. The bond to the parent moiety is through the oxygen.

"Aralkoxy" means an aralkyl-O— group. Non-limiting example of a suitable aralkoxy group is benzyloxy. The bond to the parent moiety is through the oxygen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Alkoxycarbonylalkylenyl" means an alkyl-O—CO-alkylenyl group. Non-limiting examples of suitable alkoxycarbonylalkylenyl include ethoxycarbonylmethylenyl and methoxycarbonylmethylenyl. The bond to the parent moiety is through the alkylenyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylheteroaryl" means an alkyl-heteroaryl- group in which the heteroaryl and alkyl are as previously described. The bond to the parent moiety is through the heteroaryl.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Arylsulfinyl" means an aryl-S(O)— group. The bond to the parent moiety is through the sulfinyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Heteroaralkylthio" means a heteroaralkyl-S— group in which the heteroaralkyl group is as previously described. The bond to the parent moiety is through the sulfur.

"Heteroarylsulfinyl" means an heteroaryl-S(O)— group. The bond to the parent moiety is through the sulfinyl.

"Heteroarylsulfonyl" means a heteroaryl-S($O_2$)— group. The bond to the parent moiety is through the sulfonyl.

"Heteroarylthio" means a heteroaryl-S— group in which the heteroaryl group is as previously described. The bond to the parent moiety is through the sulfur.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and other animals.

The term "optionally substituted" means optional substitution with the specified groups, radicals or moieties. It should also be noted that any heteroatom with unsatisfied valences in the text, schemes, examples, structural formulae, and Tables herein is assumed to have the hydrogen atom or atoms to satisfy the valences.

The terms "at least one" compound or "one or more compounds" means one to three compounds, preferably one compound.

When any variable (e.g., aryl, heterocycle, $R^2$, etc.) occurs more than once in any substituent or in Formula I, its definition at each occurrence is independent of its definition at every other occurrence. Also, combinations of substituents and/or variables are permissible only if such combinations result in stable compounds.

The compounds of Formula I can be administered as racemic mixtures or enantiomerically pure compounds within the scope of the present invention.

As used herein, the term "composition" is intended to encompass a product comprising the specified ingredients in the specified amounts, as well as any product which results, directly or indirectly, from combination of the specified ingredients in the specified amounts.

The compounds of formula I can form salts, solvates and prodrugs which are also within the scope of this invention. Reference to a compound of formula I herein is understood to include reference to salts, solvates and prodrugs thereof, unless otherwise indicated.

Solvates of the compounds of the invention are also contemplated as within the scope of the present invention. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" and the like, is intended to equally apply to the salt and solvate of enantiomers, stereoisomers, rotamers, tautomers or racemates of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect.

A preferred dosage is about 0.001 to 100 mg/kg of body weight/day of the compound of Formula I. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula I, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human)

a. an amount of a first compound, said first compound being a compound of Formula I, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of Formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of Formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1 B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula I can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:

CH$_3$CN means acetonitrile;
MeOH means methanol;
TFA means trifluoroacetic acid;
DCE means dichloroethane;
Dppf means diphenylphosphinoferrocene;
DCM means dichloromethane;
DIEA means N,N diisopropylethylamine;
DMF means N,N-dimethylformamide;
DMSO means methyl sulfoxide;
9-BBN means 9-borabicyclo[3.3.1]nonane;
EDCL means 1-(3-dimethylaminopropyl)-3-ethylcarbodiimide hydrochloride;
HOBT means 1-hydroxybenzotriazole hydrate;
Boc means Butoxycarbonyl;
NMR means nuclear magnetic resonance spectroscopy;
LCMS means liquid chromatography mass spectrometry;
AcOEt or EtOAc means ethyl acetate;
HRMS means high resolution mass spectrometry;
room temperature or rt (ambient) means about 25° C.;
NaBH(OAc$_3$) means sodium triacetoxyborohydride.

Alternative mechanistic pathways and analogous structures within the scope of the invention would be apparent to those skilled in the art.

EXPERIMENTAL EXAMPLES

The following examples illustrate the preparation of some of the compounds of the invention and are not to be construed as limiting the scope of the invention disclosed herein.

Compounds of type Ia are prepared according to Scheme 1:

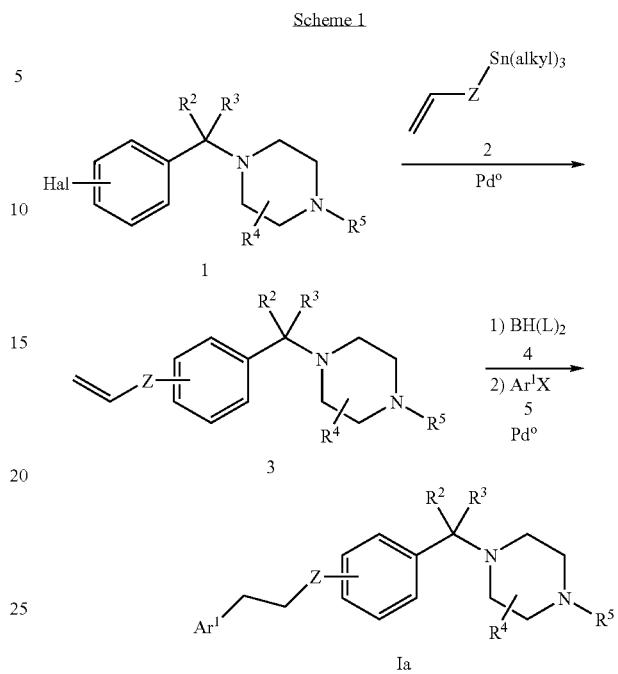

Compound 1, where Hal is halo, preferably bromo or iodo, is prepared according to WO 00/66558 and U.S. Pat. No. 6,391,865. Compound 1 is treated with a vinyl stannane 2, where Z is a bond or an alkylene group, in the presence of a palladium catalyst to give olefin 3. This is hydroborated with 4 and the resulting borane is treated with an aryl halide 5, where Ar$^1$ is aryl or heteroaryl as previously defined such that Ar$^1$ and Z together form a group R$^1$ as previously defined, in the presence of a palladium catalyst to give 1b.

Compounds of type Ib can be prepared according to Scheme 2:

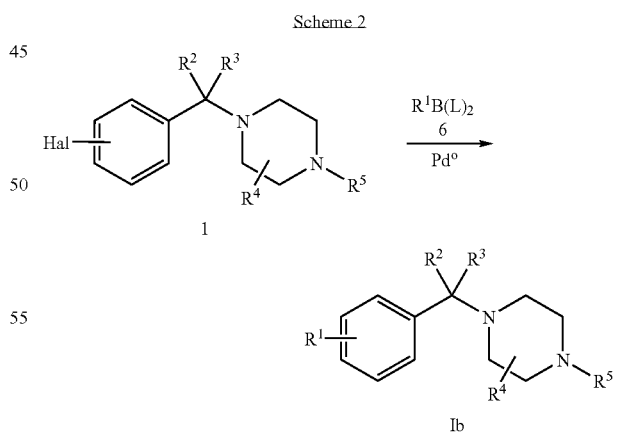

Compound 1 is treated with a borane or boronic acid derivative 6, and L is H or any of a variety of ligands on boron such as alkyl, OH or alkoxy, in the presence of a palladium catalyst to give Ia.

Compounds of this invention can be prepared directly according to the methods described above. Alternatively, one compound of this invention can be transformed to another compound of this invention by functional group manipulations well known to those skilled in the art. For instance, for compounds where

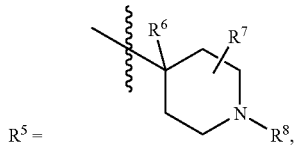

and R⁸ is a boc group, the boc group can be removed by treatment with an acid such as TFA to give the N—H derivative (R⁸=H) and a new R⁸ group can be introduced using well-known methods as described below.

PREPARATION OF INTERMEDIATES

Preparation A: 1-tert-butoxycarbonyl-4-{4-[1 (S)-(4-Bromophenyl)-ethyl]-3(R)-methylpiperazin-1-yl}-piperidine

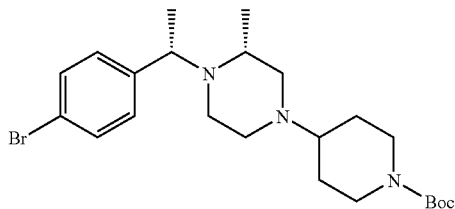

Step 1

Methyl S-lactate (5.0 g) in CH₂Cl₂ (40 ml) was stirred at −70° C. with trfluoromethanesulfonic anhydride (7.6 ml) and 2,6-lutidine (7.8 ml). The cooling was removed and the mixture stirred for 0.5 h and washed with 2N HCl. The organic phase was added to (S)-methyl 4-bromobenzylamine (9.0 g) and K₂CO₃ (11.2 g) in water (60 ml). The mixture was stirred 20 h at RT, the organic phase was separated and dried over K₂CO₃, evaporated and chromatographed on silica gel with Et₂O—CH₂Cl₂ to give the desired product (7.50 g) as a thick oil.

Step 2

The product of step 1 (7.5 g)-was heated at reflux in 1,2-dichloroethane (40 ml) and chloroacetyl chloride (5.0 ml) for 5 h, then evaporated and the resultting residue was used directly in the next step.

Step 3

The product of step 2 was dissolved in DMSO (80 ml), water (10 ml), cooled in an ice bath, and NaI (8 g) was added. Concentrated NH₄OH solution (15 ml) was added and the mixture was stirred for 20 h while coming to RT. Water (200 ml) was added dropwise, and the solids were collected, washed well with water and dried at 700 C./5 mm to give the diketopiperazine, suitable for the next step.

Step 4

To a mixture of the product of step 3 (6.8 g), 1,2-dimethoxyethane (60 ml) and NaBH₄ (3.4 g) under N₂, was added BF₃.OEt₂, (6.8 ml) dropwise, and the mixture was heated at 100° C. for 10 h. After cooling to RT, CH₃OH (20 ml) was added dropwise, followed by conc. HCl (30 ml). The mixture was heated at 100° C. for 1 h., cooled, basified with excess 2N NaOH and extracted with EtOAc. The organic layer was dried over K₂CO₃ and evaporated to obtain 1-[1-(4-Bromo-phenyl)-ethyl]-2-methyl-piperazine (5.85 g), suitable for the next step.

Step 5

The product of step 4 was stirred for 20 h. at RT with N-Boc-4-piperidinone (4.32 g), HOAC (1.15 ml), CH₂Cl₂ (80 ml) and sodium triacetoxy-borohydride (NaBH(OAc)₃) (8.3 g). Thereafter the reaction was quenched with excess aqueous Na₂CO₃ solution slowly and stirred for 0.5 h. The organic layer was separated and filtered through a pad of silca gel, washing with 10:1 CH₂Cl₂-Et₂O to elute all of the product. The filtate was evaporated and dissolved in Et₂O (100 ml). To this was added dropwise a 4M solution of HCl in 1,4-dioxane (10 ml). The solids were collected, washed with Et₂O, and stirred with CH₂Cl₂ and excess aqueous NaOH. The organic phase was dried over K₂CO₃ and evaporated to obtain 1-tert-butoxycarbonyl-4-{4-[1 (S)-(4-bromophenyl)-ethyl]-3(R)-methylpiperazin-1-yl}-piperidine (5.45 g).

Preparation B: 1-tert-butoxycarbonyl-4-{4-[1 (S)-(4-Bromophenyl)-ethyl]-3(R)-methylpiperazin-1-yl}-4-methylpiperidine

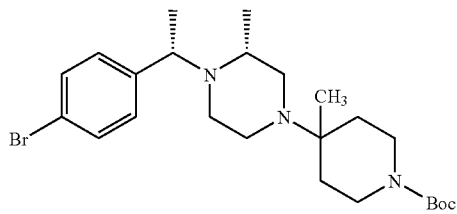

The product of Preparation A, step 4 (1.0 g), 4-tert-butyoxycarbonyl-4-piperidinone (0.77 g) and TiCl₄ (1.0 g) in 15 mL CH₂Cl₂ was stirred for 20 h at RT, heated at reflux for 3H, then cooled to room temperature. To this was added 4.2 mL of a 1 M solution of diethylaluminum cyanide in toluene, and the resulting mixture was stirred for 5 days at room temperature. The mixture was partitioned between CH₂CL₂ and water, washed with sodium hydroxide, dried over sodium sulfate, and evaporated. The residue was chromatographed over silica gel eluting with 10;1 CH₂Cl₂-methanol to yield 0.72 g of the desired product.

Preparation C: 4-{4-[1 (S)-(4-Bromophenyl)-ethyl]-3(R),5(R)-dimethylpiperazin-1-yl}-piperidine (C-1) and 4-{4-[1(R)-(4-Bromophenyl)-ethyl]-3(R),5(R)-dimethylpiperazin-1-yl}-piperidine (C-2)

Isomer C-1

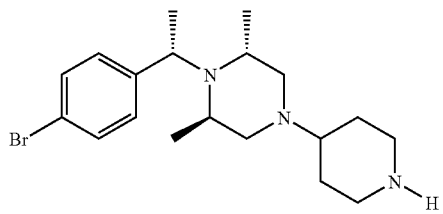

Isomer C-2

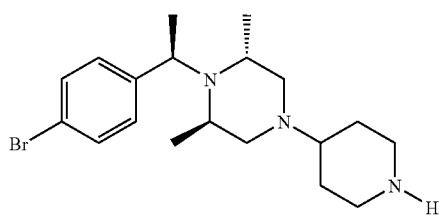

Step 1

A solution of 4-bromobenzaldehyde (1.14 g, 6.15 mmol) and 4-benzyl-(2R,6R)-dimethylpiperazine (1.20 g, 5.85 mmol) in DCM (8 mL) is treated with titanium (IV) isopropoxide (1.90 mL, 6.25 mmol) and stirred 48 h at RT. The solution is diluted with THF (8 mL) and treated with methylmagnesium bromide 3 N in Et2O (5 mL, 15 mmol) at RT. The reaction is then stirred 45 min at 40 C then poured into aqueous saturated NH4Cl, extracted with DCM, dried over Na2SO4 and concentrated. The residue is purified over silica gel (eluting with hexanes/AcOEt 94:6) to afford, in order of elution 260 mg of isomer 1 and 1.28 g of isomer 2.

Step 2

A solution of isomer 1 from Step 1 (260 mg, 0.67 mmol) in DCE (1.5 mL) is treated with 1-chloroethylchloroformate (91 uL, 0.84 mmol) at 0 C then refluxed for 2 h. The residue obtained after concentration is treated with MeOH (3 mL), refluxed for 45 min then concentrated. The residue is taken up in aqueous 1N NaOH, extracted with DCM, dried over $Na_2SO_4$ and concentrated to provide 183 mg of product C-1. Isomer C-2 is prepared in a similar manner.

Preparation D: 1-tert-butoxycarbonyl-2-methyl-4-{4-[1 (S)-(4-Bromophenyl)-ethyl]-3(R)-methylpiperazin-1-yl}-piperidine

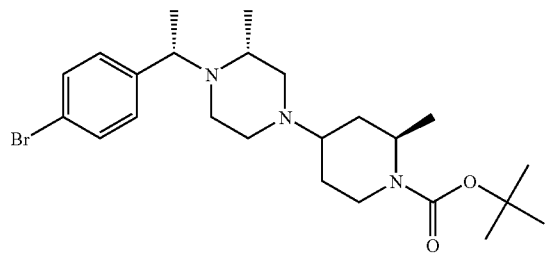

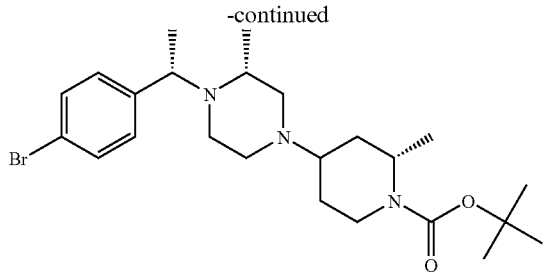

Step 1:

A solution of 0.52 g of 7-Methyl-1,4-dioxa-8-aza-spiro [4.5]decane-8-carboxylic acid tert-butyl ester), prepared according to the method of Beak at al. (J. Org. Chem. 1993,58,1109-1117), in 6 ml acetic acid and 2.5 ml concentrated HCl was stirred overnight at room temperature. The mixture was diluted with ethyl acetate and washed with 1N sodium hydroxide. The organic layer was dried over sodium sulfate and evalorated to give 0.29 g of a yellow oil. This was dissolved in 15 ml ether and treated with 5 ml 1N NaOH and 72 g (2.57 mmol) boc anhydride. The mixture was stirred for 3 hours at room temperature then diluted with ether and washed with 1N NaOH, water, and brine. The organic layer was dried over sodium sulfate and evaporated. The residue was purified by column chromatography over silica gel, eluting with 20% ethyl acetate in hexane to give 0.18 g of 1-tert-butoxycarbonyl-2-methyl-4-oxo-piperidine as a mixture of diastereomers.

Step 2:

1-[1-(4-Bromo-phenyl)-ethyl]-2-methyl-piperazine (0.104 g) from preparation A step 4 was treated with 0.075 g 1-tert-butoxycarbonyl-2-methyl-4-oxo-piperidine from the previous step as described in preparation A step 5 to afford 1-tert-butoxycarbonyl-2-methyl-4-{4-[1 (S)-(4-Bromophenyl)-ethyl]-3(R)-methylpiperazin-1-yl}-piperidine.

EXPERIMENTAL EXAMPLES

Experiment 1

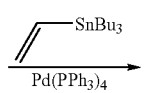

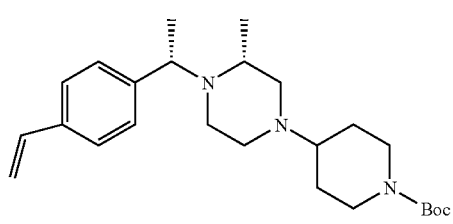

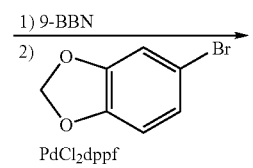

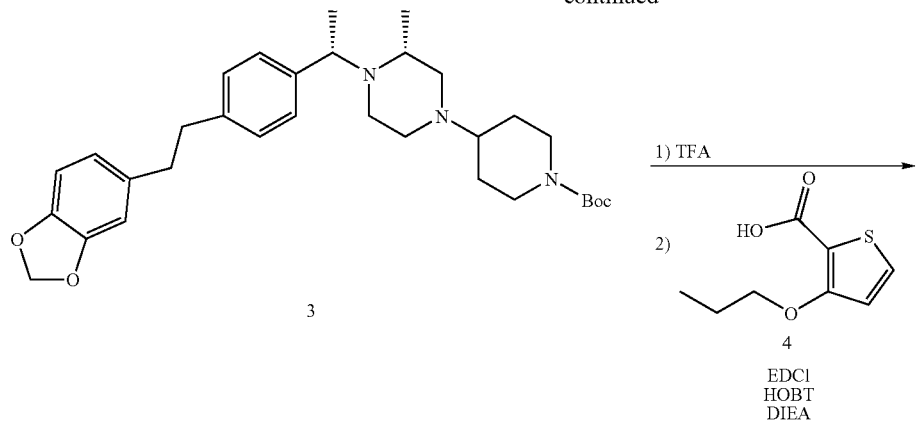

3

1) TFA

2) 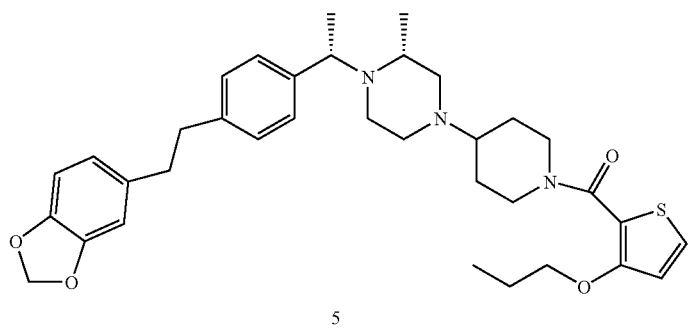
4

EDCl
HOBT
DIEA

5

Step 1: A solution of 885 mg (1.9 mmol) of Compound 1, prepared as described in above in 20 ml toluene was treated with 722 mg (2.3 mmol) tributyl vinyl tin and 44 mg (0.04 mmol) tetrakis(triphenylphosphine)palladium(0). The resulting mixture was heated at reflux overnight. An additional 0.5 mg of tributyl vinyl tin and 20 mL toluene was added and the solution refluxed an additional 72 hours. After cooling, the mixture was diluted with ethyl acetate, washed with water and brine, dried over sodium sulfate, and evaporated. The residue was purified by medium pressure flash chromatography, eluting with 1L dichoromethane followed by 1L 5% methanol in dichloromethane to give 915 mg of crude compound 2 which was used directly in step 2.

Step 2: To a solution of the product of step 1 in 20 ml THF was added 7.6 mL of 0.5M 9-BBN in THF and the mixture was heated at reflux for 4 hours. Another 7.6 mL of 0.5M 9-BBN was added and the mixture was heated at reflux for another 4 hours. After cooling to room temperature, the mixture was treated with a solution of 806 mg (3.8 mmol) $K_3PO_4$ in 3 ml water, a solution of 458 mg (2.3 mmol) 5-Bromo-benzo[1,3]dioxole in 3 ml DMF, and 78 mg (0.09 mmol) palladium(II) chloride-dppf complex. The resulting mixture was heated overnight at reflux, cooled to room temperature and diluted with ethyl acetate. The solution was washed with water and brine, dried over sodium sulfate, and evaporated. The residue was purified by medium pressure flash chromatography eluting with 4L 3:1 ethyl acetate:hexane to give 380 mg of compound 3.

Step 3: The boc-protected compound 3 (380 mg) was stirred with 1.1 ml of trifluoroacetic acid in 10 mL dichloromethane at room temperature for 3 hours. The solvent was removed under vacuum and the residue was dissolved in dichloromethane and washed with 1-0% sodium hydroxide. The organic layer was dried over sodium sulfate and evaporated to give 359 mg of free amine, which was used without purification. To a solution of 26 mg (57.9 mmol) of this amine in 1 mL dichloromethane was added 22 mg (115.8 mmol) of 3-Propoxy-thiophene-2-carboxylic acid 4, 22 mg (115.8 mmol) EDCI, 16 mg (115.8 mmol) HOBT, and 0.1 mL DIEA. The resulting mixture was stirred overnight at room temperature, washed with water and 10% sodium hydroxide, dried over sodium sulfate, and evaporated. The residue was purified by flash chromatography eluting with 100% ethyl acetate to give 19 mg (54% yield) of 5. NMR:

High resolution mass spec: Calculated for $C_{35}H_{46}N_3O_4S$ 604.3209. Found: 604.3212.

Using similar methods the following compounds were prepared:

| Ex | Structure | HRMS | LCMS-(M + 1)+ | LCMS RT (Min) |
|---|---|---|---|---|
| 19 | 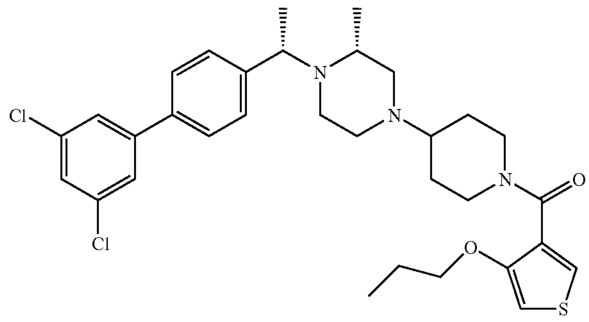 | | 600.1 | 5.51 min |
| 15 | 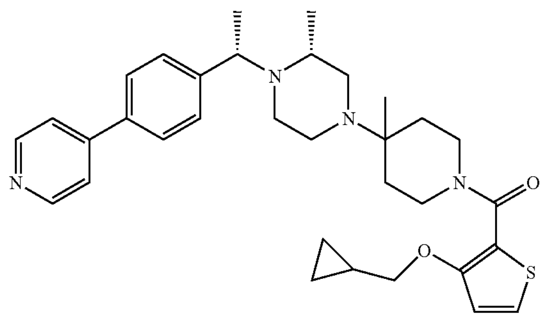 | Calc'd for C33H43N4O2S: 559.3106 Found: 559.3107 | 559.1 | 3.56 |
Experiment 2
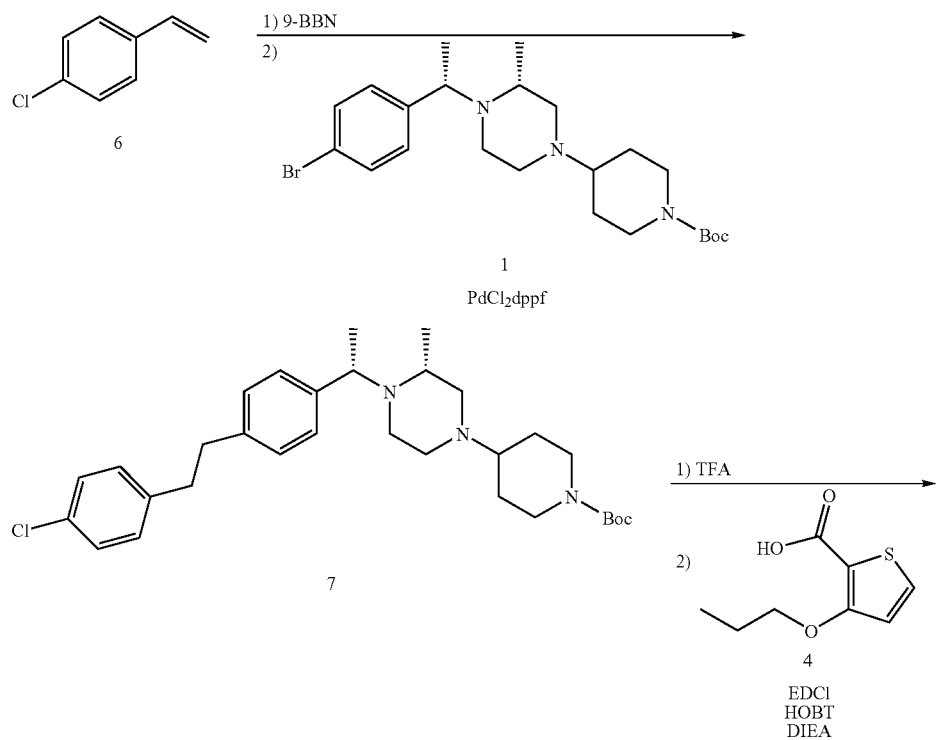

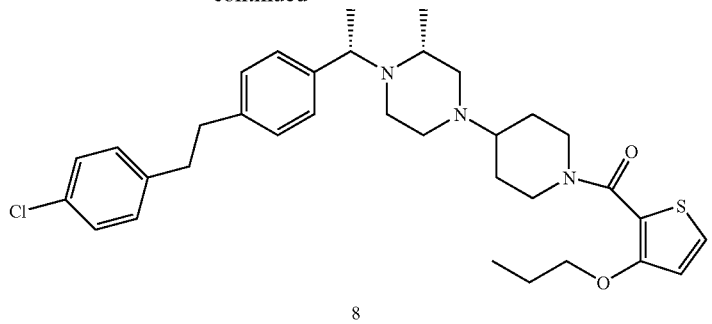

8

Step 1: A solution of 297 mg (2.1 mmol) of 1-Chloro-4-vinyl-benzene 6 in 2 ml THF was treated with 8.6 ml of 0.5M 9-BBN in THF and the mixture was heated at reflux for 4 hours. After cooling, the solution was treated with a 250 mg (0.54 mmol) of bromide 1 in 2 ml DMF, 0.75 ml of 3M aqueous $K_3PO_4$, and 87 mg (0.12 mmol) palladium(II) chloride-dppf complex. The mixture was heated at reflux overnight, cooled to room temperature, diluted with ethyl acetate, washed with water and brine, dried over sodium sulfate, and evaporated. The residue was purified by flash chromatography eluting with 5 to 28% acetone in dichloromethane to give 138 mg of compound 7.

Step 2: A solution of 10 mg (0.023 mmol) of the product of step 1 was converted to compound 8 by treatment with trifluoroacetic acid followed by coupling of the resulting amine with 3-Propoxy-thiophene-2-carboxylic acid 4 as described in Experiment 1, step 3. The product was purified by flash chromatography eluting with 100% ethyl acetate to give 9.4 mg of compound 8. NMR. High resolution mass spec: Calculated for $C_{34}H_{45}N_3O_2SCl$ 594.2921. Found: 594.2916.

Using similar methods the following compounds were prepared:

| Ex | Structure | HRMS | LCMS-(M + 1)+ | LCMS RT (Min) |
|---|---|---|---|---|
| 13 | 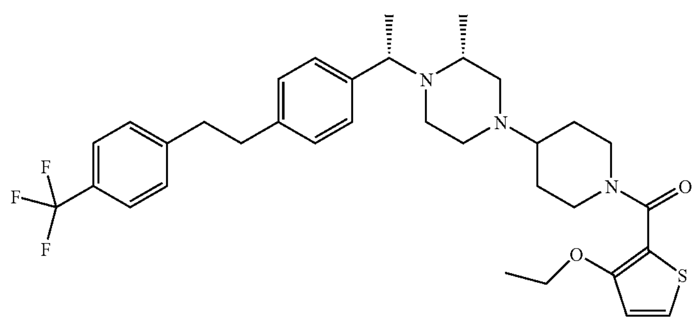 | Calc'd for C34H43F3N3O2 S: 614.3028 Found: 614.3042 | | |
| 14 | 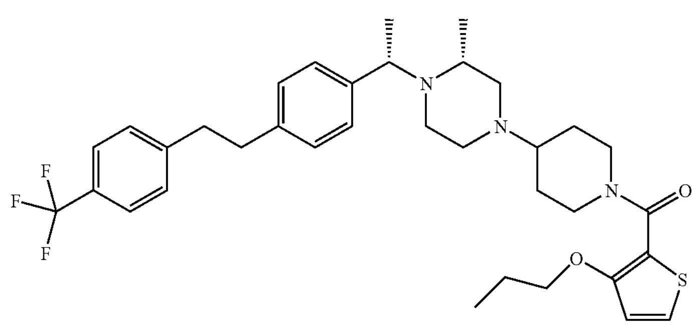 | Calc'd for C35H45F3N3O2 S: 628.3184 Found: 628.3191 | | |

Experiment 3

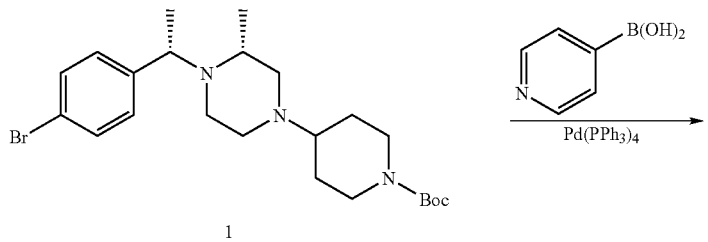

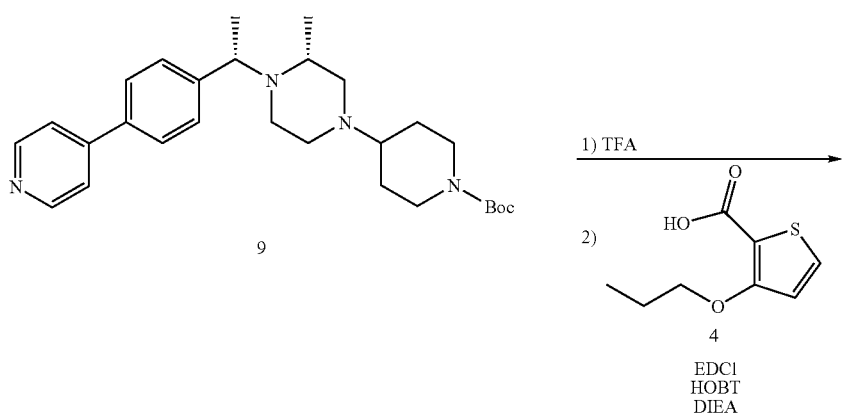

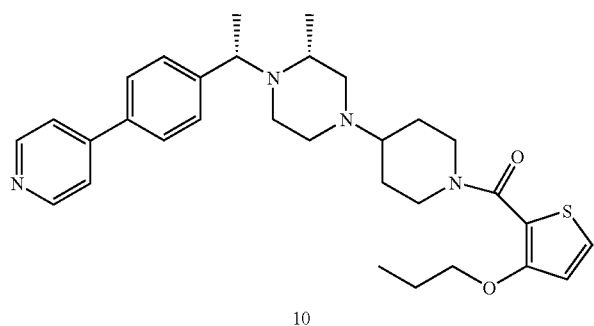

Step 1: A solution of 299 mg (0.64 mmol) of compound 1 in 2 ml DMF was treated, with 158 mg (1.28 mmol) 4-pyridylboronic acid, 407 mg (1.92 mmol) $K_3PO_4$ in 0.65 ml water, and 37 mg (0.032 mmol) tetrakis(triphenylphosphine)palladium(0). The mixture was heated at 80° C. overnight, cooled to room temperature, diluted with diethyl ether, washed with 10% sodium hydroxide, dried over magnesium sulfate, filtered through celite, and concentrated under vacuum. The residue was purified by medium pressure flash chromatography eluting with 30%-50% acetone in dichloromethane to give 121 mg of compound 9.

Step 2: The product of step 1 was treated with trifluoroacetic acid followed by coupling with 3-Propoxy-thiophene-2-carboxylic acid 4 as described in Experiment 1, step 3. The product was treated with ethereal HCl to give 86 mg of compound 10 as its hydrochloride salt. NMR LCMS High resolution mass spec: Calculated for $C_{31}H_{41}N_4O_2SI$ 533.2950. Found: 533.2944 LCMS (M+1)$^+$=533.1 (3.81 min) Using similar methods the following compounds were prepared:

| Ex | Structure | HRMS | LCMS-(M + 1)+ | LCMS RT (Min) |
|---|---|---|---|---|
| 3 | 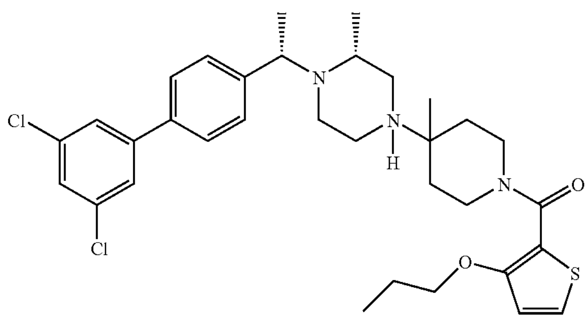 | Calc'd for C₃₃H₄₂Cl₂N₃O₂S 614.2375 Found: 614.2379 | | |
| 5 | 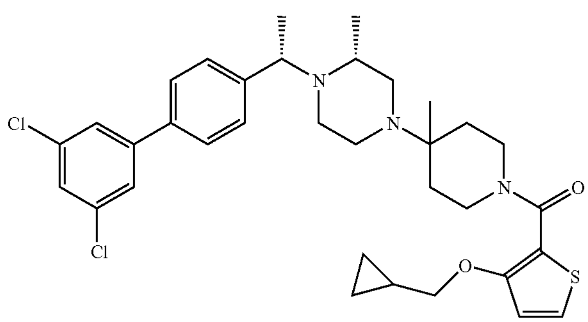 | Calc'd for C₃₄H₄₂Cl₂N₃O₂S 626.2375 Found: 626.2367 | | |
| 11 | 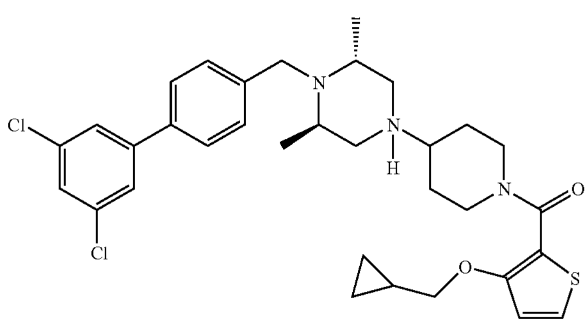 | Calc'd for C₃₃H₄₀Cl₂N₃O₂ 612.2218 Found: 612.2214 | | |
| 18 | 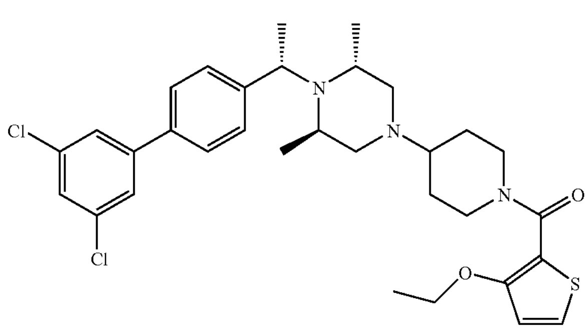 | Calc'd for C₃₂H₄₀Cl₂N₃O₂S 600.2218 Found: 600.2212 | | |

-continued

| | | | |
|---|---|---|---|
| 16 | (structure) | 600.1 | 6.26 |
| 17 | (structure) | 600.1 | 6.22 |
| 10 | (structure) | Calc'd for C29H37ClN3O2S2: 558.2015 Found: 558.2008 | |
| 2 | (structure) | Calc'd for C31H38Cl2N3O2S: 586.2062 Found: 586.2055 | |
| 6 | (structure) | Calc'd for C32H40Cl2N3O2S: 600.2218 Found: 600.2218 | |

-continued
| | | |
|---|---|---|
| 12 | 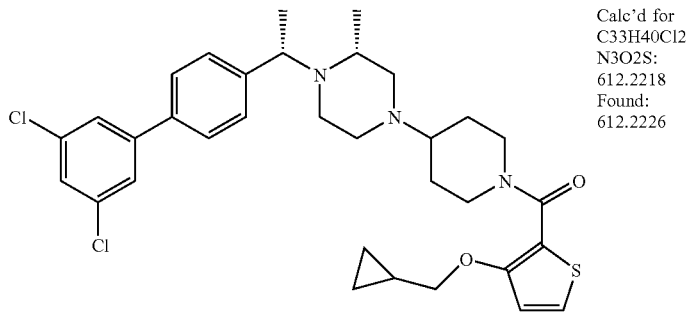 | Calc'd for C33H40Cl2N3O2S: 612.2218 Found: 612.2226 |
| 7 | 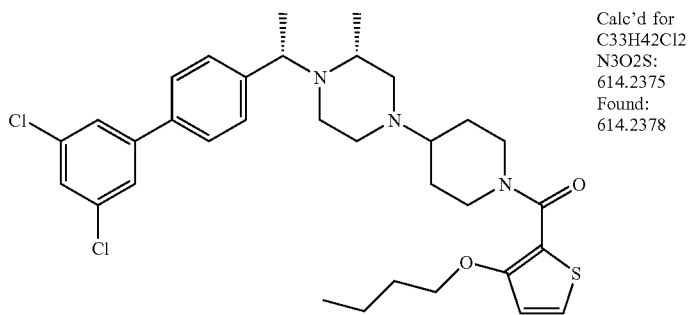 | Calc'd for C33H42Cl2N3O2S: 614.2375 Found: 614.2378 |
| Ex | Structure | NMR |
|---|---|---|
| 9 | 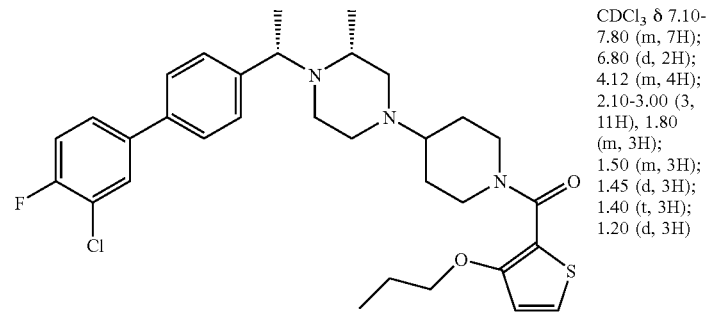 | CDCl₃ δ 7.10-7.80 (m, 7H); 6.80 (d, 2H); 4.12 (m, 4H); 2.10-3.00 (3, 11H), 1.80 (m, 3H); 1.50 (m, 3H); 1.45 (d, 3H); 1.40 (t, 3H); 1.20 (d, 3H) |
Experiment 4
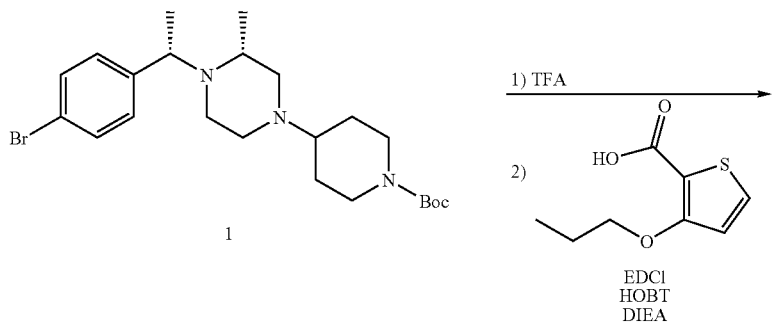

-continued

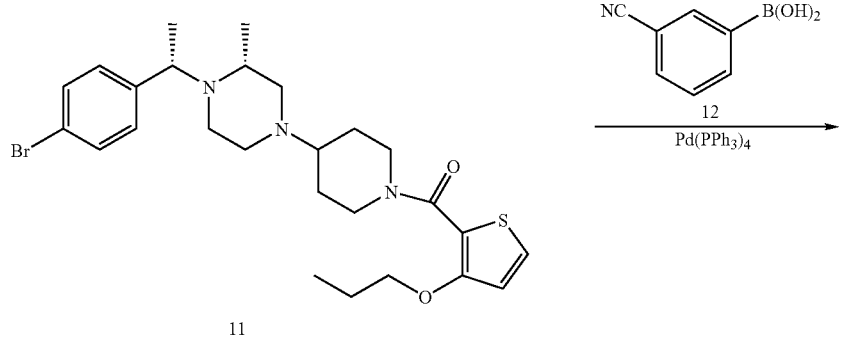

11

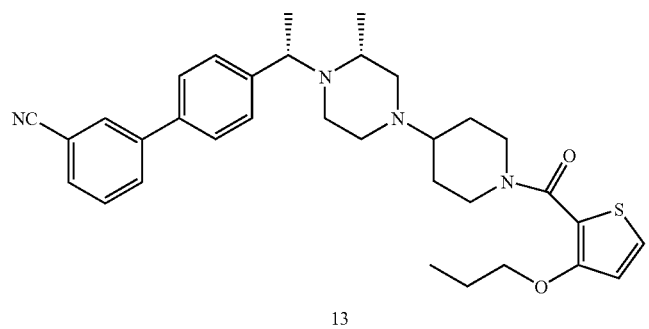

13

Compound 1 (975 mg, 2.1 mmol) is treated with TFA and the resulting N—H compound is esterified with acid 4 as described in Experiment 1, step 3 to give 573 mg amide 11.

A solution of 50 mg (0.094 mmol) of compound 11, 28 mg (0.187 mmol) of 3-cyanophenylboronic acid 12, 3.3 mg (0.004 mmol) bis-triphenylphosphine palladium chloride and 0.2 ml (0.28 mmol) 1.4M $K_2PO_4$ in 1 ml DMF was stirred at 80° C. overnight. After cooling, the mixture was diluted with ether, washed with 10% sodium hydroxide and with water, dried over sodium sulfate, and evaporated. The residue was purified by flash chromatography eluting with 100% ethyl acetate to give the product. HRMS Calc'd for $C_{33}H_{41}N_4O_2S$: 557.2950 Found: 557.2950. LCMS: LCMS $(M+1)^+=558$ (4.77 min).

MCH Receptor Binding Assay:

Membranes from CHO cells expressing the MCH receptor were prepared by lysing cells with 5 mM HEPES for 15 min at 4 C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates were then analyzed in a TOPCOUNT microplate scintillation counter (Packard). Data was analyzed and Ki values were determined using GraphPad Prim.

The compounds of Formula I exhibit MCH receptor antagonizing activity, which has been correlated with pharmaceutical activity for treating disorders such as obesity and hyperphagia, and diabetes, as well as eating disorders generally.

For the compounds of this invention, a range of MCH receptor binding activity (Ki values) from about 6 nM to about 25 nM was observed.

Results for other compounds appear in the table below where the compounds are rated "A" for Ki values from 6 nM to 10 nM, "B" for Ki values greater than 10 nM to less than 15 nM and "C" for Ki values greater than 15 nM.

Preferred embodiments of the claimed compounds include Examples 16 and 20, both of which have Ki values equal to 6.

TABLE

MCH Receptor Activity

| Ex. | Structure | Activity |
|---|---|---|
| 1 | 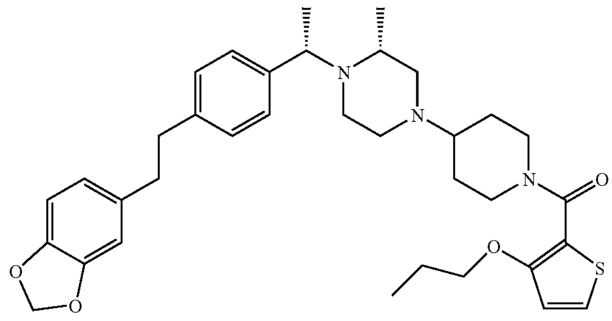 | B |
| 2 | 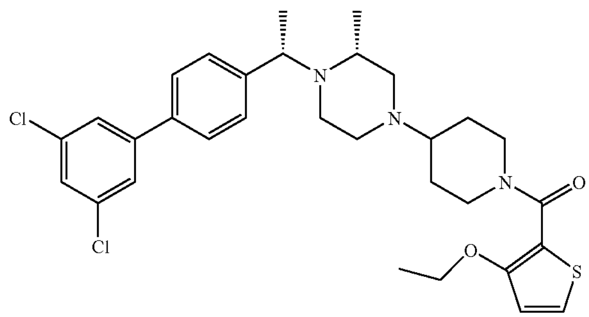 | B |
| 3 | 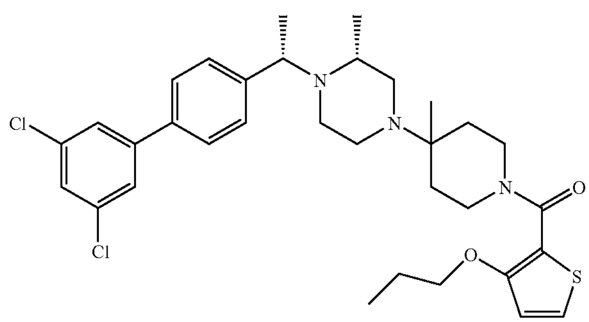 | A |
| 4 | 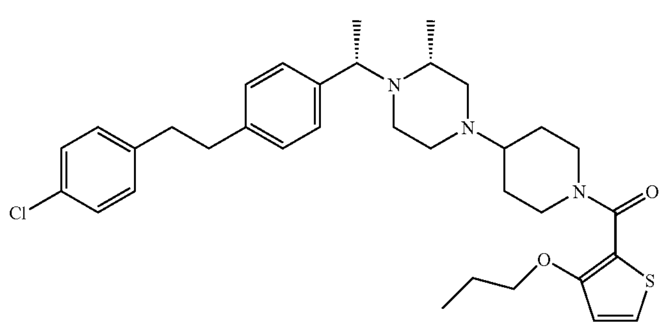 | B |

TABLE-continued
MCH Receptor Activity
| Ex. | Structure | Activity |
|---|---|---|
| 5 | 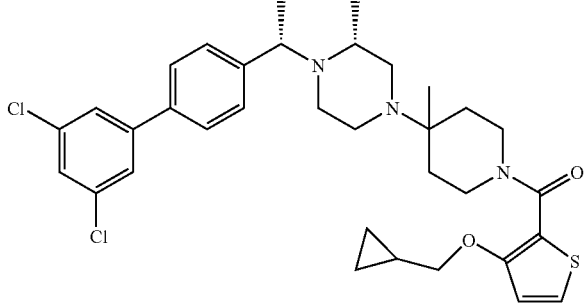 | A |
| 6 | 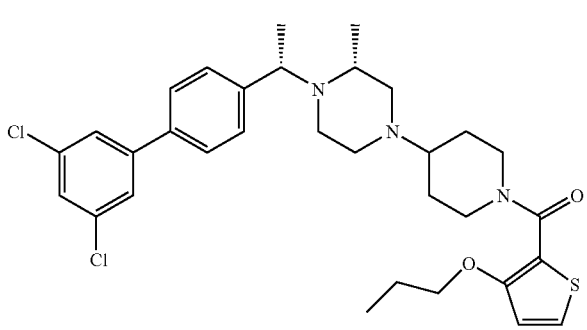 | A |
| 7 | 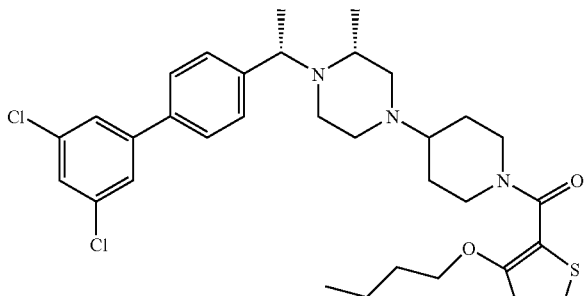 | B |
| 8 | 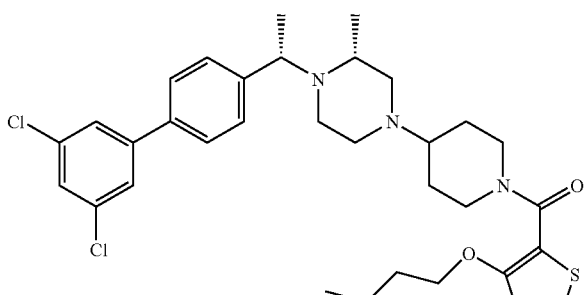 | A |

TABLE-continued
MCH Receptor Activity
| Ex. | Structure | Activity |
|---|---|---|
| 9 | 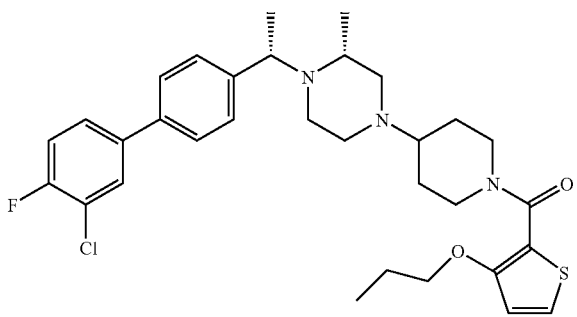 | B |
| 10 | 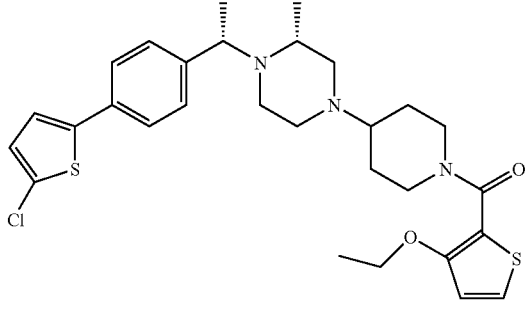 | C |
| 11 | 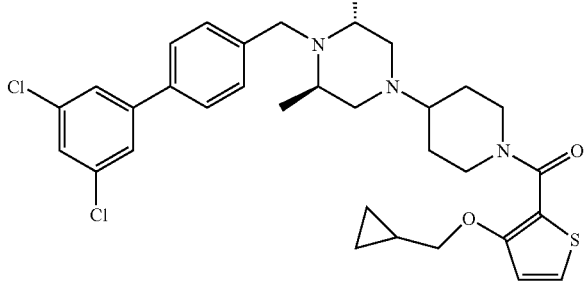 | C |
| 12 | 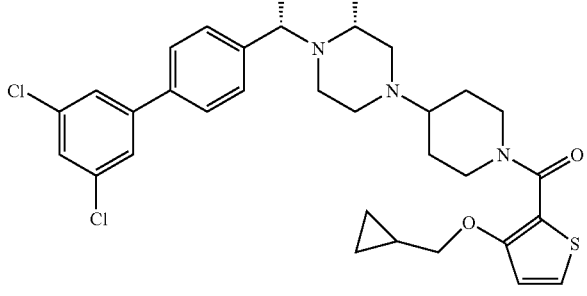 | A |

TABLE-continued

MCH Receptor Activity

| Ex. | Structure | Activity |
|-----|-----------|----------|
| 13  | 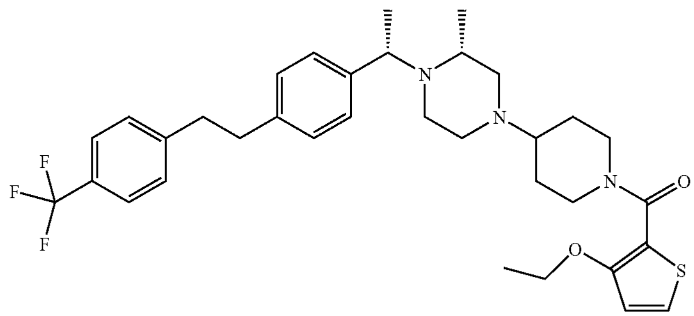          | A        |
| 14  | 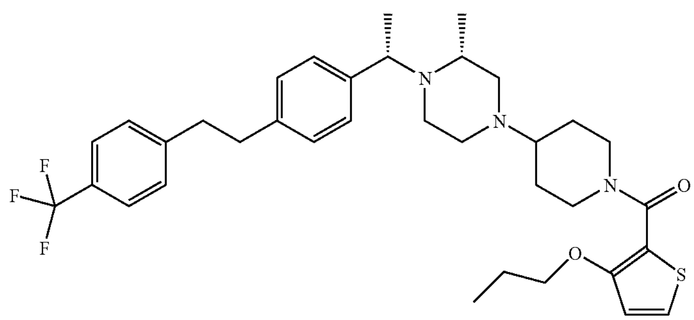          | A        |
| 15  | 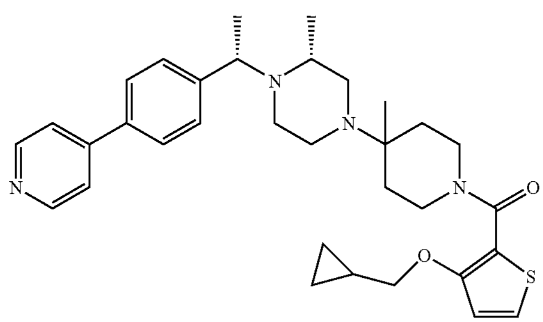          | A        |
| 16  | 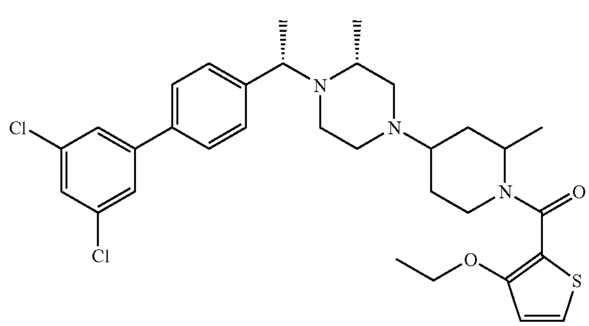          | A        |

TABLE-continued

MCH Receptor Activity

| Ex. | Structure | Activity |
|---|---|---|
| 17 | 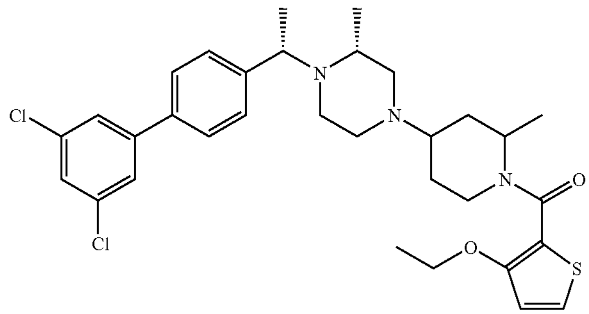 | C |
| 18 | 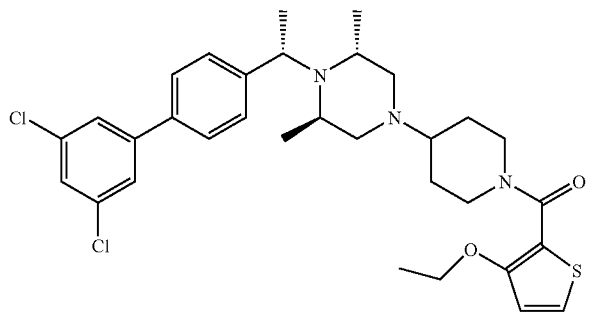 | B |
| 19 | 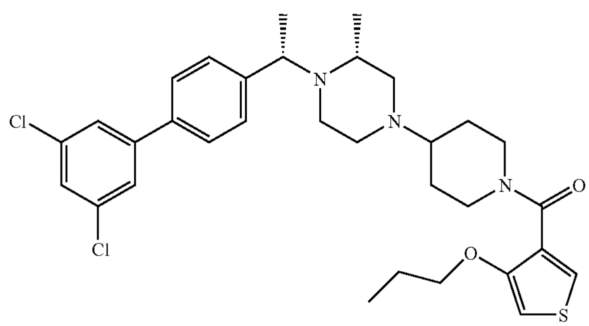 | A |
| 20 | 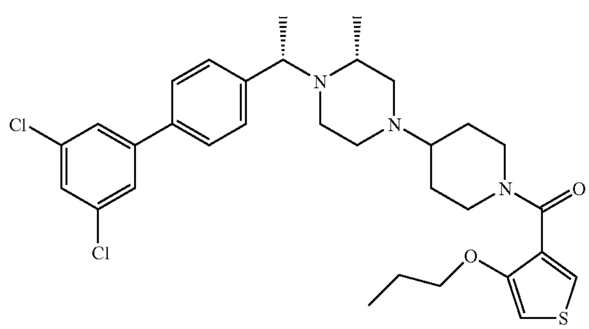 | A |

What is claimed is:
1. A compound of the formula
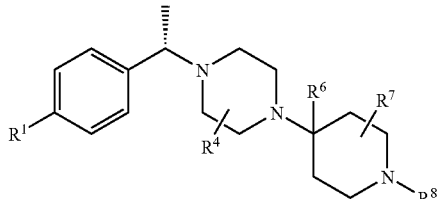
wherein
R¹ is selected from the group consisting of
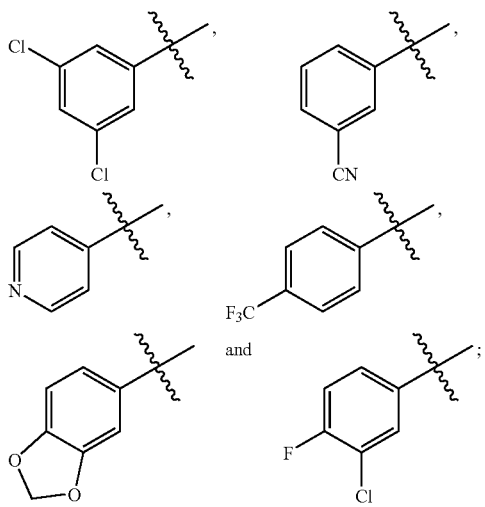
R⁴, R⁶ and R⁷ are methyl;
R⁸ is —C(O)R⁹;
R⁹ is
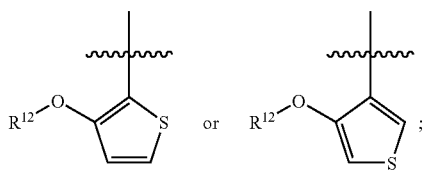
and
R¹² is ethyl, propyl, butyl or cyclopropylmethyl, or a pharmaceutically acceptable salt thereof.
2. A compound selected from the group consisting of:
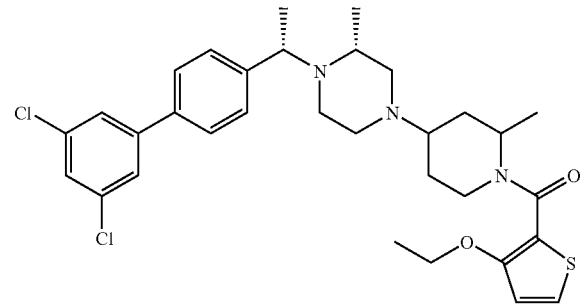
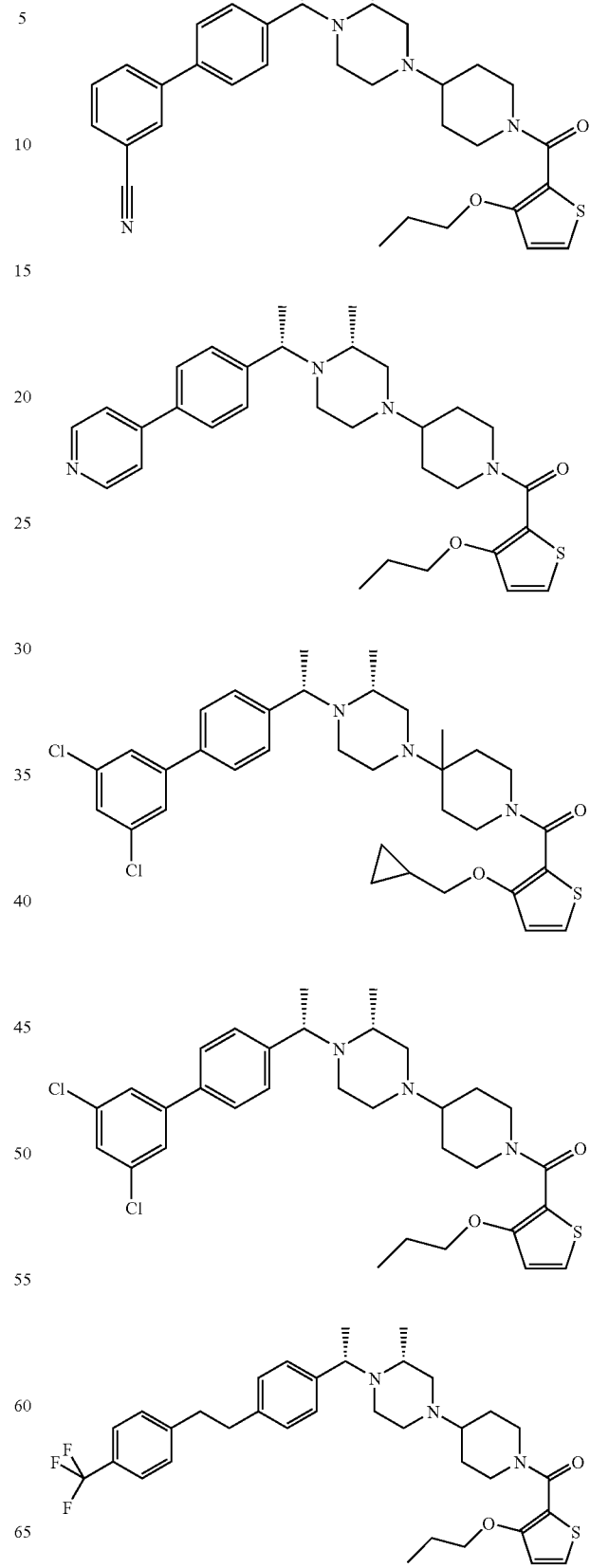

-continued
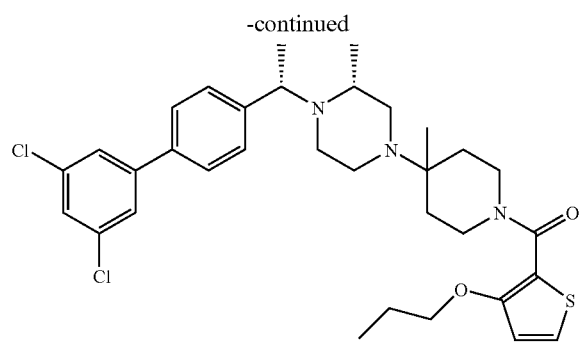
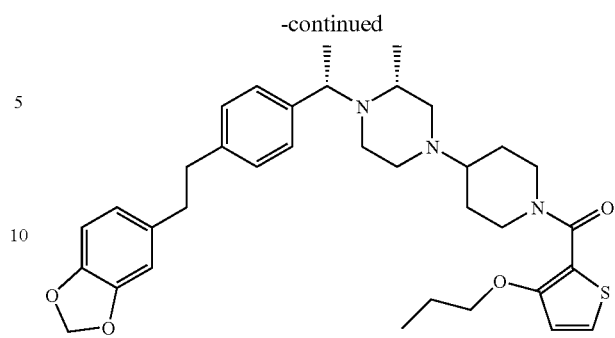
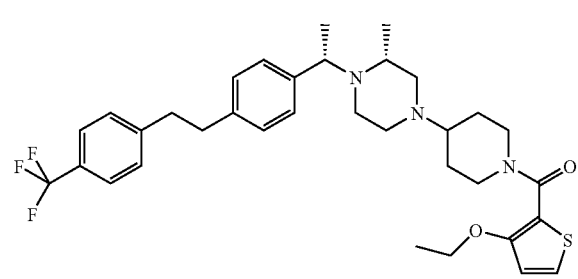
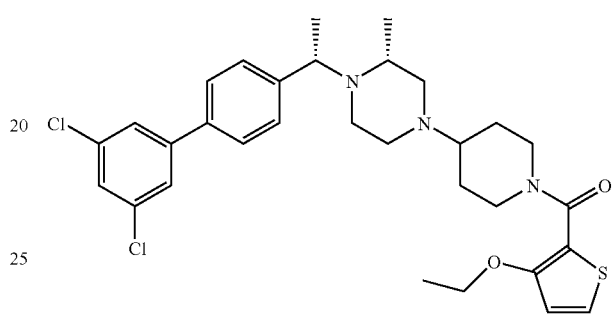
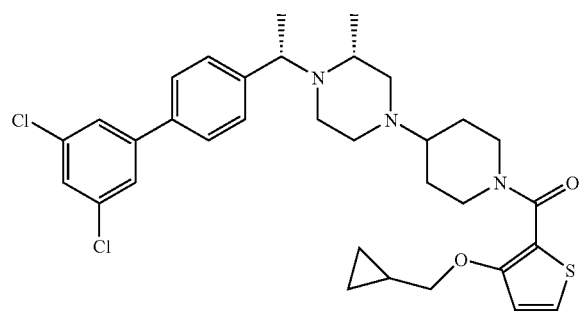
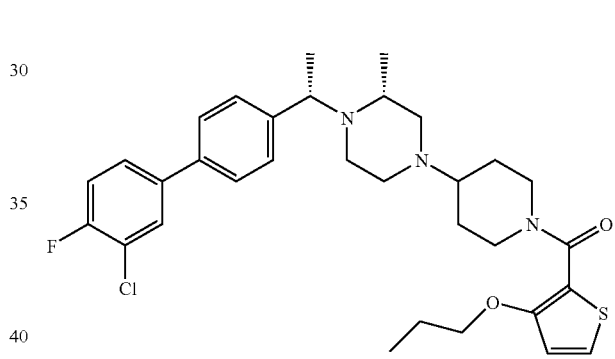
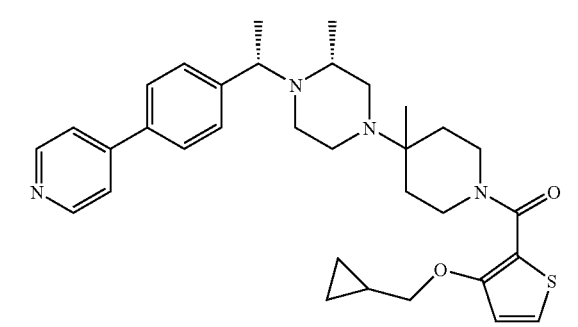
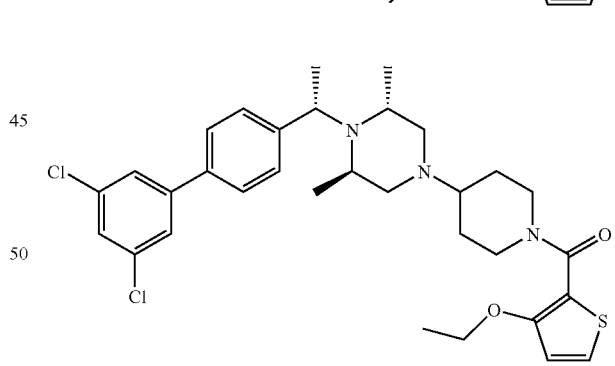
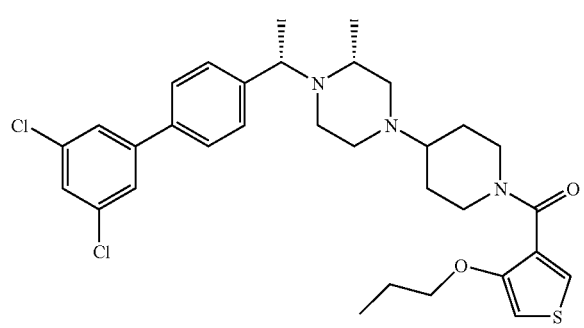
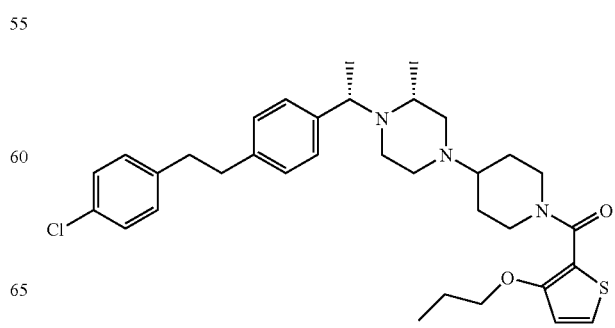

-continued

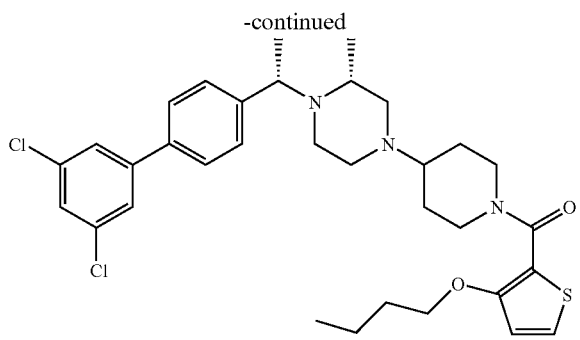

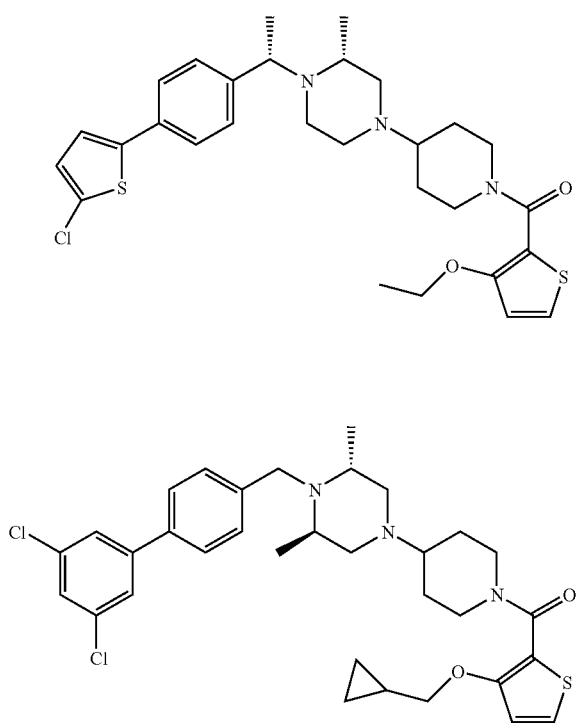

and

-continued

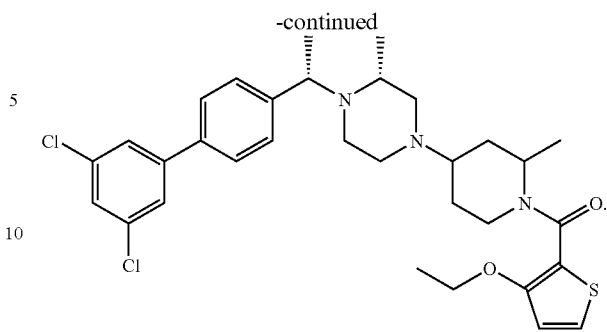

or a pharmaceutically acceptable salt thereof.

3. A pharmaceutical composition which comprises a therapeutically effective amount of:
   a first compound, said first compound being a compound of claim 2, or a pharmaceutically acceptable salt of said compound;
   a second compound, said second compound being an antiobesity and/or anorectic agent selected from the group consisting of a $\beta_3$ agonist, a thryomimetic agent, an anorectic agent and NPY antagonist; and
   a pharmaceutically acceptable carrier.

4. A pharmaceutical composition which comprises a therapeutically effective amount of:
   a first compound, said first compound being a compound of claim 2, or a pharmaceutically acceptable salt of said compound;
   a second compound, said second compound selected from the group consisting of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin, an insulin mimetic, metformin, acarbose, troglitazone, rosaglitazone, pioglitazone, GW-1929, a sulfonylurea, glipazide, glyburide, and chlorpropamide; and
   a pharmaceutically acceptable carrier.

5. A pharmaceutical composition comprising a therapeutically effective amount of at least one compound of claim 2, or a pharmaceutically acceptable salt thereof, in combination with at least one pharmaceutically acceptable carrier.

6. A process for making a pharmaceutical composition comprising combining at least one compound of claim 2, or a pharmaceutically acceptable salt thereof, and at least one pharmaceutically acceptable carrier.

* * * * *